US00PP36996P2

(12) United States Plant Patent
NeSmith et al.

(10) Patent No.: US PP36,996 P2
(45) Date of Patent: Oct. 7, 2025

(54) BLUEBERRY PLANT NAMED 'CBG-23-04'

(50) Latin Name: *Vaccinium corymbosum*
Varietal Denomination: CBG-23-04

(71) Applicants: Rio Vista Farms Inc., Selma, CA (US); University of Georgia Research Foundation, Inc., Athens, GA (US)

(72) Inventors: D. Scott NeSmith, Griffin, GA (US); Gregory Willems, Kingsbury, CA (US)

(73) Assignees: Rio Vista Farms Inc., Selma, CA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 18/885,153

(22) Filed: Sep. 13, 2024

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — Knobbe, Martens, Olson & Bear, LLP

(57) ABSTRACT

The new variety of blueberry 'CBG-23-04' is characterized by having large, firm, berries that ripen early in the season and have a long shelf life. Further, the berries of the new variety 'CBG-23-04' are crunchy with a very sweet, floral taste.

10 Drawing Sheets

Latin name of the genus and species claimed: *Vaccinium corymbosum.*

Variety denomination: 'CBG-23-04'.

REFERENCE TO RELATED APPLICATIONS

This application is related to U.S. application Ser. No. 18/884,792, filed Sep. 13, 2024, U.S. application Ser. No. 18/884,644, filed Sep. 13, 2024, U.S. application Ser. No. 18/884,736, filed Sep. 13, 2024, and U.S. application Ser. No. 18/885,323, filed Sep. 13, 2024, which are directed to blueberry varieties developed by the same program.

BACKGROUND AND SUMMARY OF THE INVENTION

Disclosed herein is a new and distinct southern highbush blueberry variety (*Vaccinium corymbosum*). The varietal denomination of the new variety is 'CBG-23-04'.

The new variety 'CBG-23-04' is a product of a hand-pollinated cross of seed parent 'TH-1492' (unpatented) and pollen parent 'TH-1870' (unpatented) made by D. Scott NeSmith in 2019 in Griffin, Georgia. The new variety 'CBG-23-04' was germinated from seed. The date of first planting of the new variety 'CBG-23-04' was November 2021. The new variety 'CBG-23-04' was selected by Gregory Willems in May 2023 in Reedley, California. Subsequent testing has demonstrated that the combination of traits disclosed herein that characterize the new variety are stable and retained true to type through successive generations of vegetative, asexual reproduction in Fresno County, California.

The new variety of blueberry 'CBG-23-04' is characterized by having large, firm, berries that ripen early in the season and have a long shelf life. Further, the berries of the new variety 'CBG-23-04' are crunchy with a very sweet, floral taste. The new variety 'CBG-23-04' has not shown notable diseases or other pest problems beyond those also common for other blueberry varieties. The new variety 'CBG-23-04' has a chilling requirement of about 150-200 hours below 45° F.

The phenotype of the new blueberry variety 'CBG-23-04' may vary somewhat with variations in environment, such as temperature and light intensity, and cultural practices, without, however, any variance in genotype.

COMPARISON TO THE PARENTS

The new variety 'CBG-23-04' is distinguished from its seed parent 'TH-1492' (unpatented) in that the fruit of the new variety is firm, compared to a medium firmness for the fruit of 'TH-1492'. Further, the fruit of the new variety 'CBG-23-04' is sweeter and crunchier than the fruit of 'TH-1492'. Additionally, the fruit of the new variety 'CBG-23-04' ripens later, on about May 10$^{th}$, compared to a mid-season ripening on about May 1$^{st}$ to May 5$^{th}$ for 'TH-1492'. Lastly, the new variety 'CBG-23-04' flowers around February 26$^{th}$, compared to around February 27$^{th}$ to March 3$^{rd}$ for 'TH-1492'.

The new variety 'CBG-23-04' is distinguished from its pollen parent 'TH-1870' (unpatented) by having large to very large-sized fruit, compared to the medium to large-sized fruit of 'TH-1870'. Additionally, the fruit of the new variety 'CBG-23-04' ripens later, on about May 10$^{th}$, compared to about April 23$^{rd}$ to April 28$^{th}$ for 'TH-1870'. Lastly, the new variety 'CBG-23-04' flowers around February 26$^{th}$ compared to around February 20$^{th}$ to February 23$^{rd}$ for 'TH-1870'.

COMPARISON TO CLOSEST VARIETY

The new variety 'CBG-23-04' resembles 'Suziblue' (U.S. Plant Pat. No. 21,167) and 'Emerald' (U.S. Plant Pat. No. 12,165) in that they are early season southern highbush blueberry cultivars with the same vigor. However, the new variety 'CBG-23-04' begins flowering earlier than 'Suziblue' and later than 'Emerald' in Central California. Additionally, the new variety 'CBG-23-04' begins ripening later than 'Suziblue' and 'Emerald' in Central California. However, the new variety 'CBG-23-04' has a similar harvest period to 'Suziblue' and 'Emerald'. Further, the fruit of the new variety 'CBG-23-04' is softer than that of 'Emerald', but firmer than the fruit of 'Suziblue',

TABLE 1

TABLE 1 shows a comparison of the characteristics of 'CBG-23-04', 'Suziblue' (PP21,167) and 'Emerald' (PP12,165). Rating scales are based on 1 to 10 score, with 1 being the least desirable and 10 being the most desirable.

| | 'Suziblue' | 'Emerald' | 'CBG-23-04' |
|---|---|---|---|
| Berry Size | 8.0 | 8.0 | 9.0 |
| Berry Scar | 7.0 | 7.5 | 7.5 |
| Berry Color | 7.0 | 8.0 | 8.0 |
| Berry Firmness | 7.3 | 8.5 | 8.0 |
| Berry Flavor | 7.0 | 7.0 | 8.5 |
| Cropping | 8.5 | 8.5 | 7 |
| Plant Vigor | 8.0 | 8.0 | 8.0 |
| Date of 50% Flowering | Feb. 28 | Feb. 15 | Feb. 26th |
| Date of 50% Ripening | May 7 | May 1 | May. 10th |
| Fruit Development Period | 69 Days | 60 Days | 75 Days |

TABLE 2

TABLE 2 shows a comparison of the characteristics of the new variety 'CBG-23-04' and related varieties 'CBG-23-01', 'CBG-23-02', 'CBG-23-03' and 'CBG-23-05'.

| | 'CBG-23-04' | 'CBG-23-01' | 'CBG-23-02' | 'CBG-23-03' | 'CBG-23-05' |
|---|---|---|---|---|---|
| Season | Early to mid-season | Early | Early to mid-season | Early | Early to mid-season |
| Harvest date | May 3rd-June 1st | April 18th-May 12th | April 28th-May 28th | April 18th-May 12th | May 3rd-June 1st |
| Fruit size | Large, 18 mm-21 mm | Large, 20 mm-24 mm | Large, 19 mm-24 mm | Large, 18 mm-21 mm | Very large, 19 mm-22 mm |
| Flavor | Very sweet with mild acidity and floral undertones | Sweet, aromatic | Balanced sweetness and acidity | Balanced sweetness and acidity | Sweet with moderate acidity |
| Fruit Texture | Crisp | Smooth, crisp | Crisp, firm | Crisp | Smooth, crisp |
| Fruit Color | Medium blue | Deep blue | Medium blue | Light to medium blue | Medium blue |

BRIEF DESCRIPTION OF THE ILLUSTRATIONS

The accompanying color photographic illustrations taken in Reedley, California in 2024 pertain to 2.5 year old plants, and show the overall appearance and distinct characteristics of the new variety 'CBG-23-04'. The colors in the photographs are as true as possible but may differ slightly from the color values cited in the detailed botanical description, which accurately describes the colors of the new variety 'CBG-23-04'.

DESCRIPTION OF THE NEW VARIETY

Figure 1:
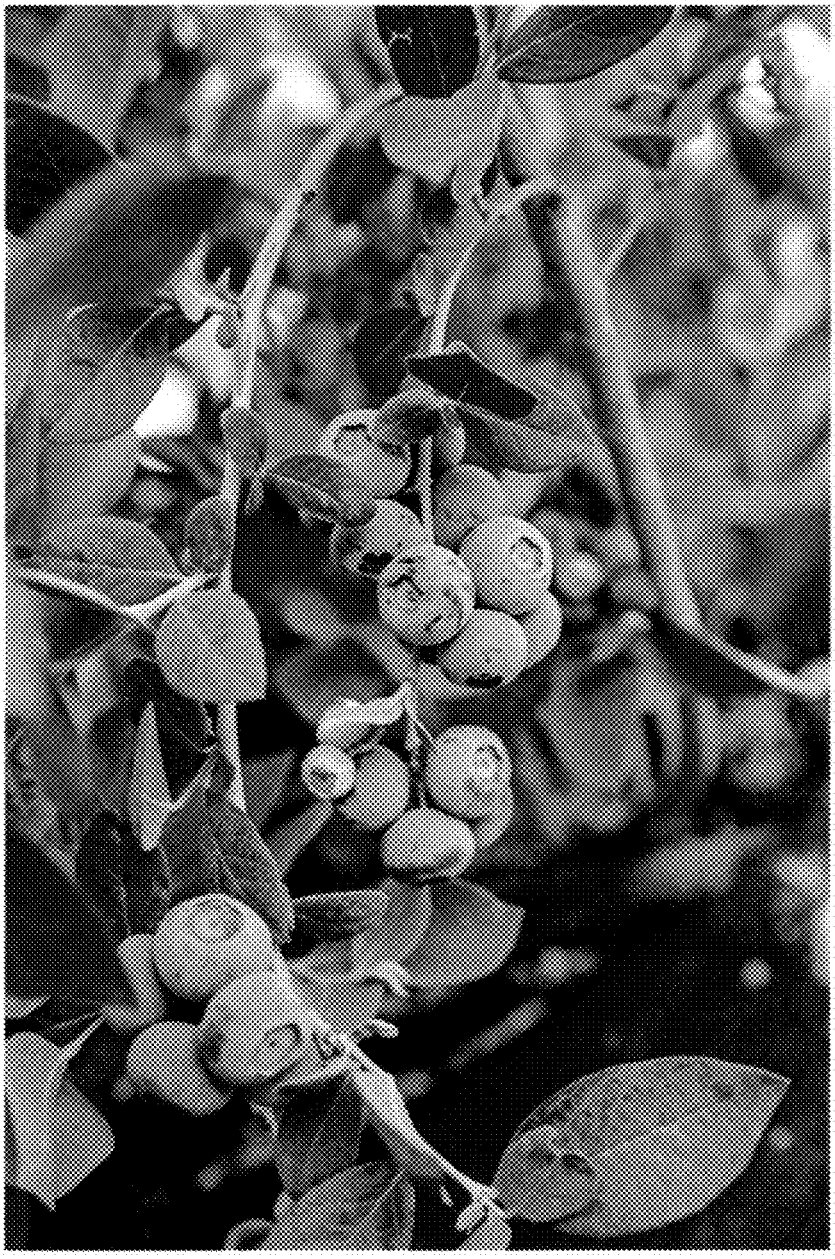
FIGS. 1-3 show the berries of the new variety 'CBG-23-04' on the plant ready for harvest.
Figure 2:
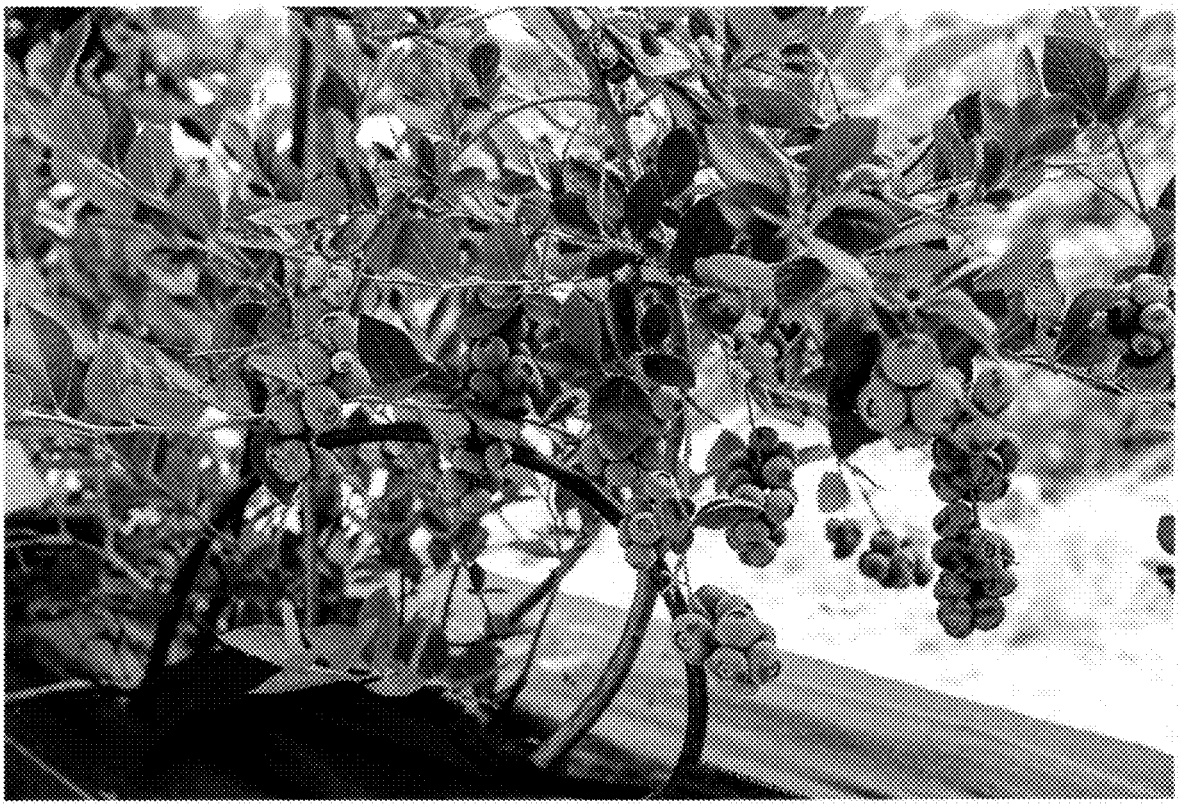
Figure 3:
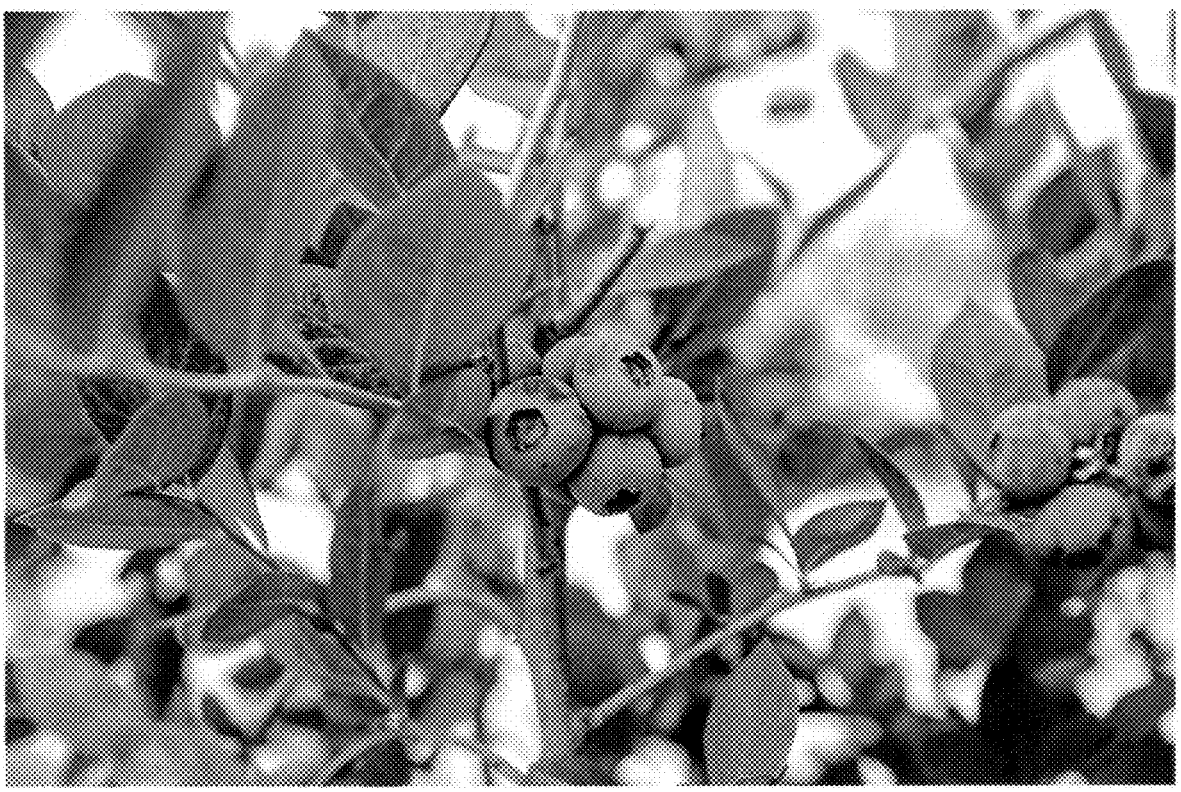
Figure 4:
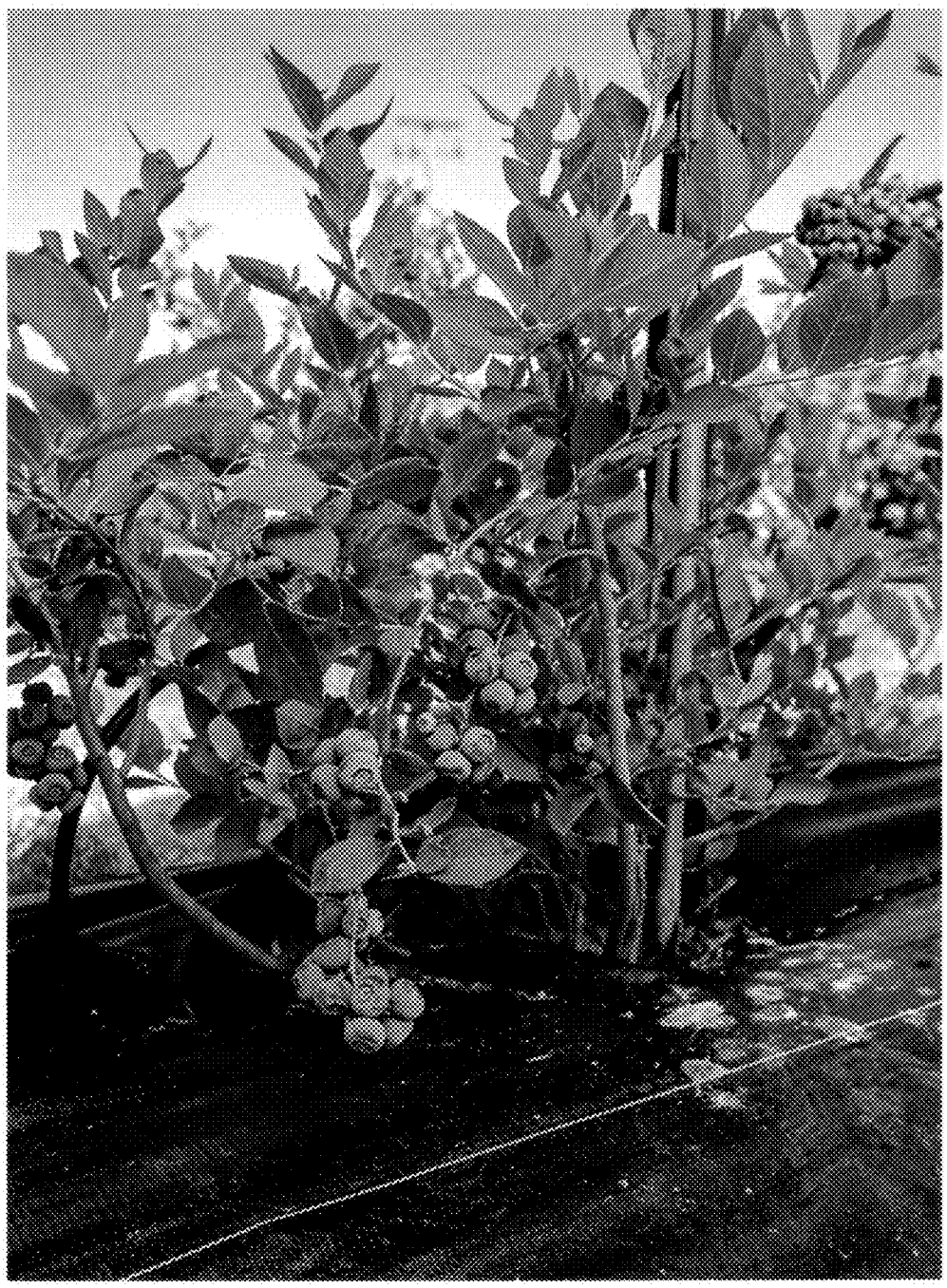
FIG. 4 shows the growth pattern of the plants of the new 'CBG-23-04'.
Figure 5:
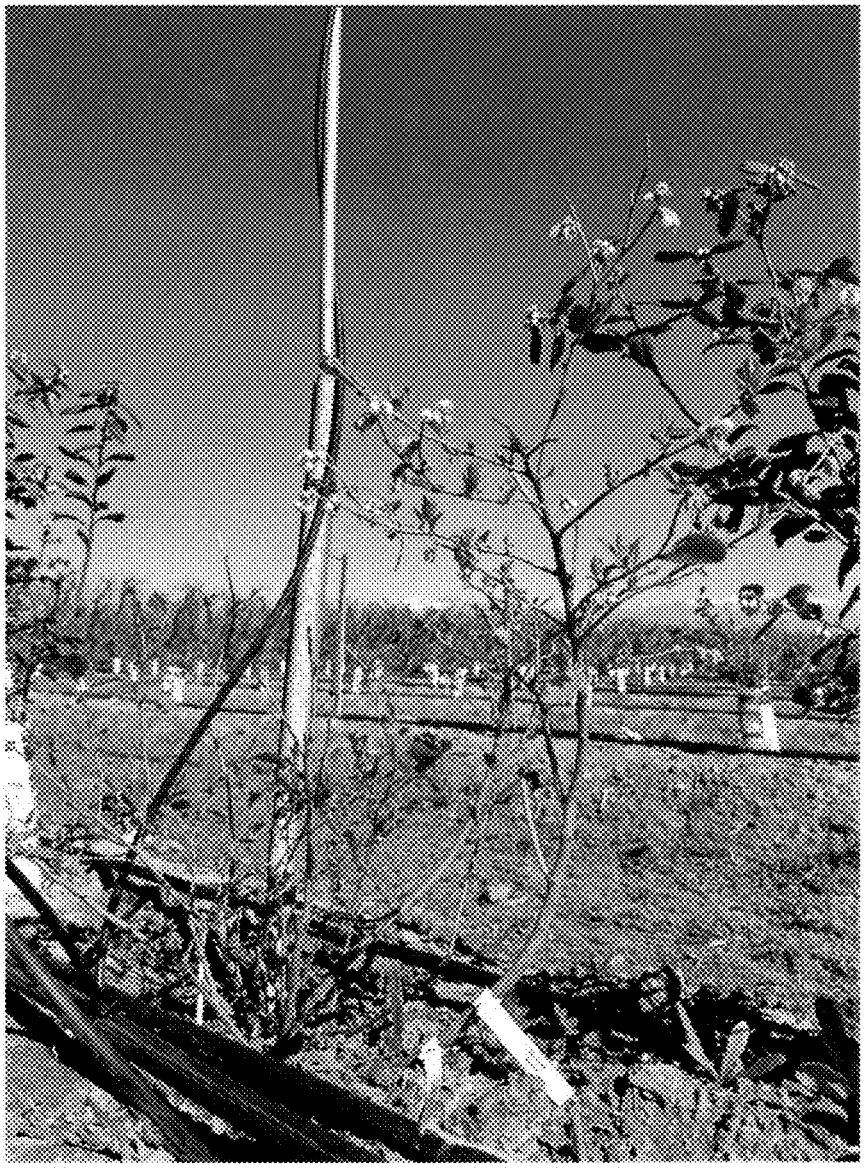
FIG. 5 shows the plants of the new variety 'CBG-23-04' during bloom.
Figure 6:
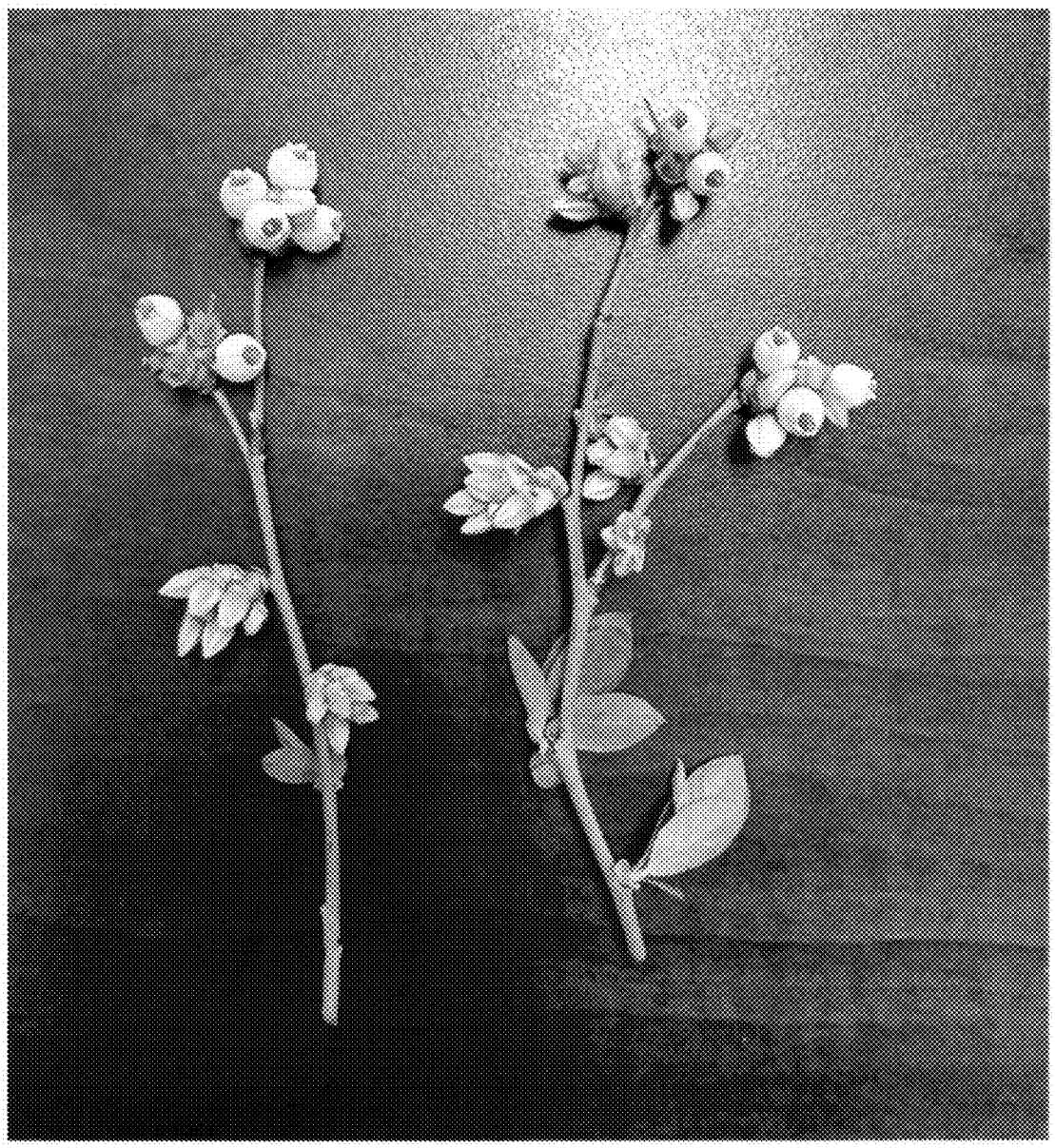
FIG. 6 shows the flowers of the plants of the new variety 'CBG-23-04'.
Figure 7:
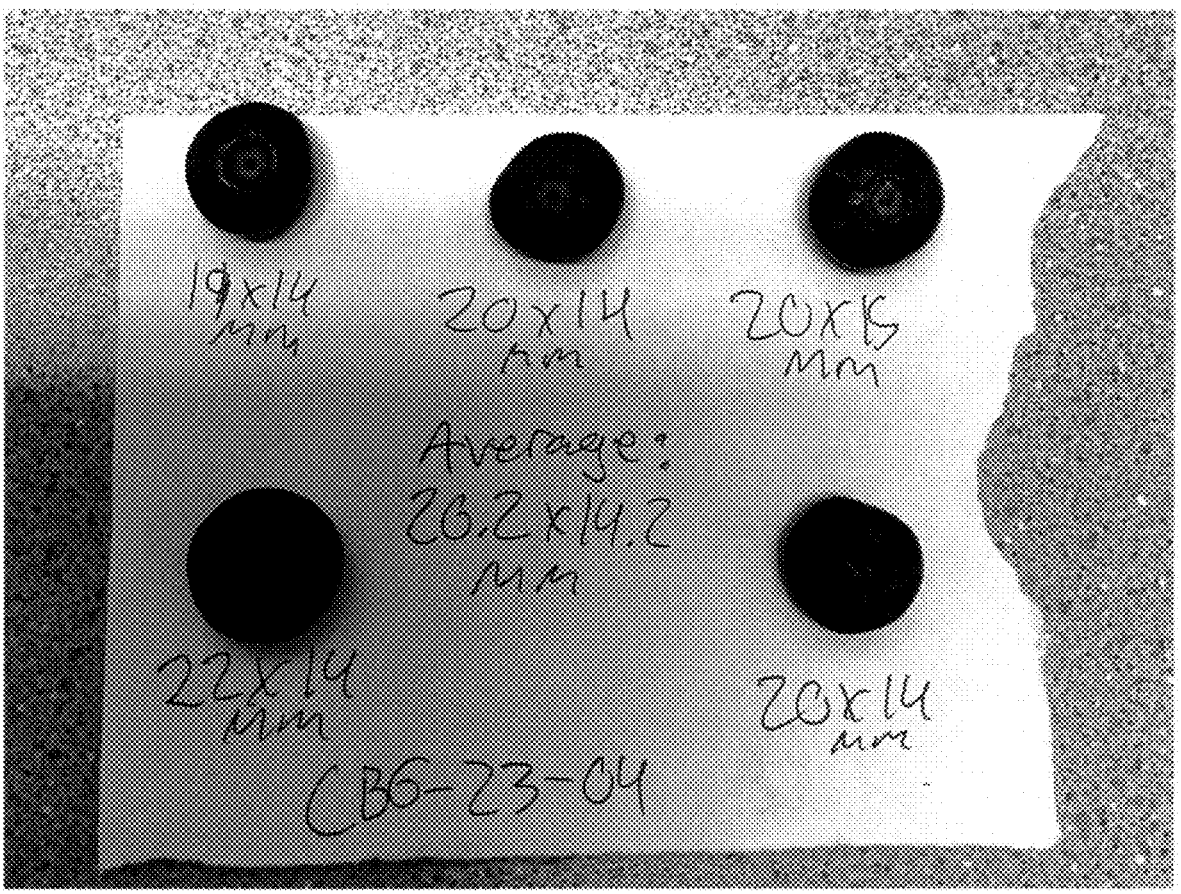
FIG. 7 shows the average berry size of the new variety 'CBG-23-04'.
Figure 8:
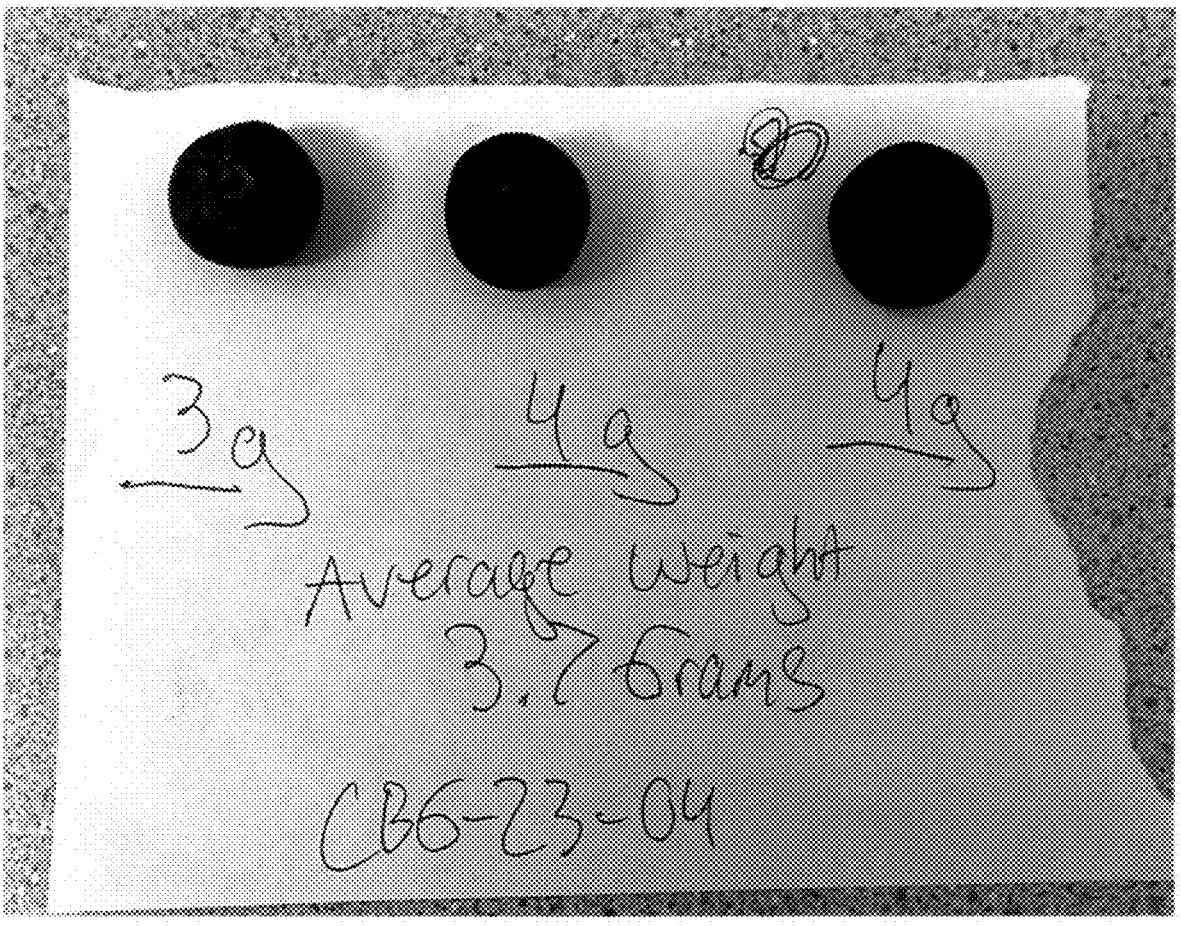
FIG. 8 shows the average berry weight of the new variety 'CBG-23-04'.
Figure 9:
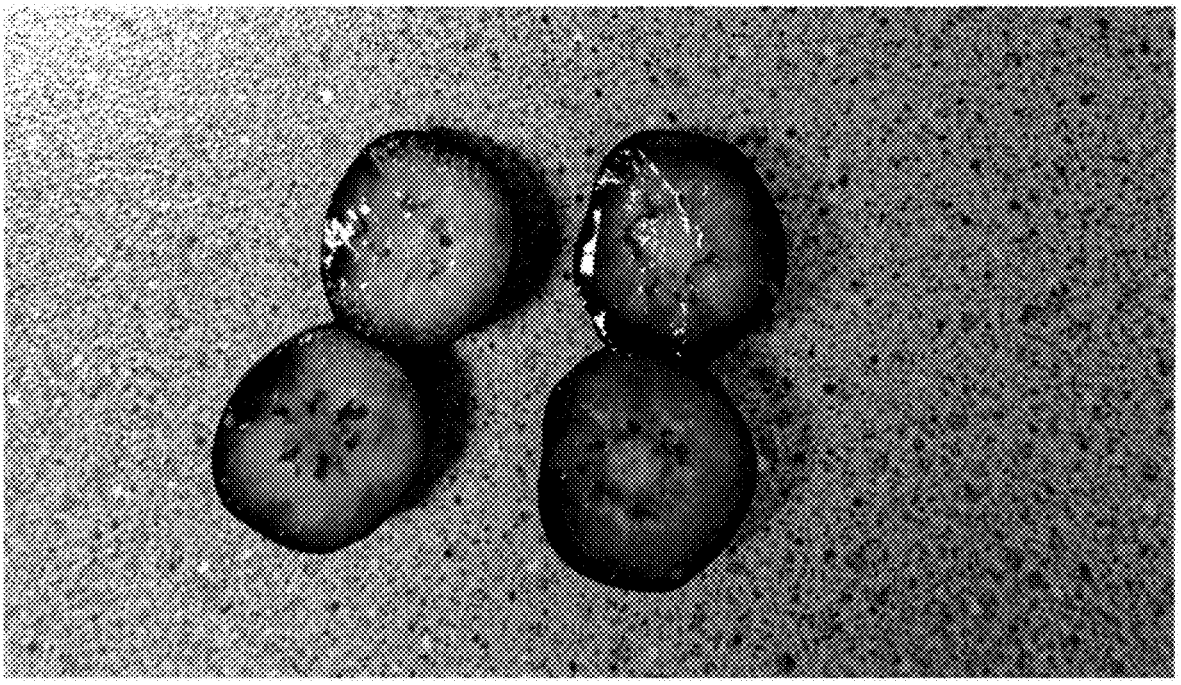
FIG. 9 shows the fruit of the new variety 'CBG-23-04' cut in half.
Figure 10:
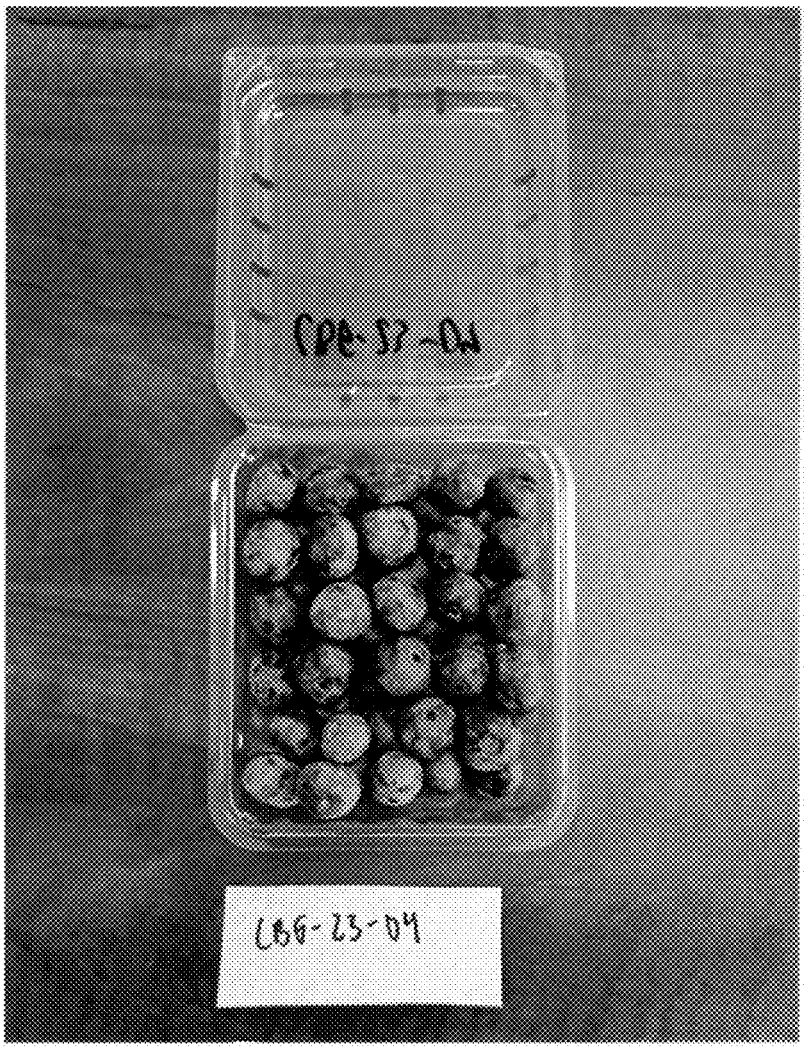
FIG. 10 shows the fruit of the new variety 'CBG-23-04' as a whole.

The following traits have been consistently observed in the original plant of the new variety 'CBG-23-04' and in asexually propagated progeny via vegetative cuttings in Fresno County, California. The descriptive matter which follows pertains to 2.5-year-old 'CBG-23-04' plants grown in the vicinity of Reedley, California during 2023, with supplemental irrigation. The dimensions, sizes, colors, and other characteristics given are to be understood to be approximations and averages set forth as accurately as practicable.

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, Sixth Edition, 2019 reprint. The colors and other phenotypic attributes may deviate from the stated values and descriptions depending upon variation in environmental, seasonal, climatic and cultural conditions.

General: The new variety 'CBG-23-04' produces fruit from about May 3$^{rd}$ to June 1$^{st}$. Measurements were taken on 2.5-year-old plants.

Plant:

*Size.*—3.0 feet tall, 10-inch plant base/crown.

*Habit.*—Tight vertical leaf growth and vertical canes, some spreading, vigorous vertical growth. Plants have 1-4 main canes with branches spreading within 20 to 25 cm of the surface of the soil.

*Productivity.*—About 1.9 pounds per plant.

*Cold hardiness.*—Similar to other early ripening southern highbush varieties in USDA Plant Hardiness Zone 9b.

*Chilling requirements.*—Approximately 150 to 200 hours of temperatures at or below 45° F. to induce normal leafing and flowering dueting the spring.

*Leafing.*—Plants readily break numerous leaf buds simultaneously with anthesis.

*Canes.*—Main Cane: Diameter: Approximately 13 mm. Color: About Medium Grey-Brown 199B. Length: Approximately 1 m to 1.4 m. Texture: Woody. First Major Branch: Diameter: Approximately 6 mm. Color: About Medium Yellow-Green N144C. Length: Approximately 0.7 m to 0.9 m. Texture: Woody. 2-year-Old Cane: Diameter: Approximately 7 mm. Color: About Medium Grey-Brown 199B. Length: Approximately 0.6 m to 0.8 m. Texture: Woody. Current Season Wood: Diameter: Approximately 6 mm. Color: About Medium Yellow-Green 144C. Length: Approximately 0.6 m to 0.8 m. Texture: Smooth.

*Fruiting wood*.—Numerous twigs approximately 15 to 25 cm in length and internode lengths of approximately 15 to 25 mm are common. The diameter is approximately 3 mm to 4 mm and the texture is smooth.

Foliage:

*Leaf color of mature leaves*.—Top side color: About Dark Green NN137A. Under side color: About Light Green 138D.

*Leaf arrangement*.—Alternate simple.

*Leaf shape*.—Elliptic.

*Leaf venation*.—Pinnate with slight netting (or slightly reticulated).

*Leaf apices*.—Broadley acuminate.

*Leaf base*.—Cuneate to acute.

*Leaf length*.—Approximately 50 to 60 mm.

*Leaf width*.—Approximately 30 to 35 mm.

*Leaf margin*.—Entire.

*Leaf surface*.—Glaucous (waxy) on the top of the leaf, while the bottom of the leaf has a smooth texture without the glaucous coating.

*Petiole size*.—Small, approximately 4 mm long and 1 mm wide.

*Petiole color*.—About Light Yellow-Green 145C.

*Petiole leaves margin*.—The leaf margin is smooth or occasionally ciliate, with stalked glands present on the petiole or along the leaf margin.

Flower:

*Date of* 50% *anthesis*.—About February 26$^{th}$ in Central California.

*Flower shape*.—Urceolate.

*Flower bud number*.—Medium (5 to 7 buds per fruiting shoot).

*Flowers per cluster*.—Approximately 4 to 5.

*Flower fragrance*.—Yes.

*Corolla*.—Color: About Medium White NN155A to Medium White NN155B for both inner and outer surfaces. Length: Approximately 6 to 7 mm. Width: Approximately 6 to 7 mm. Aperture Width: Approximately 3 to 3.5 mm.

*Peduncle*.—Length: About 10 to 17 mm. Color: About Medium Yellow-Green 144B. Diameter: Approximately 3 mm. Texture: Slightly woody

*Pedicel*.—Length: Approximately 3 to 4 mm. Color: About Light Yellow-Green 145C. Diameter: Approximately 2 to 2.5 mm. Texture: Smooth.

*Calyx*.—Calyx (with sepals) Diameter: Approximately 5 to 6 mm. Color center of calyx: About Medium Green 138B. Color of sepals: About Medium Green 138C. Average sepals per calyx: About 5. Sepal length: Approximately 3 mm. Sepal width: Approximately 2 mm.

*Stamen*.—Length: Approximately 6.5 to 7 mm. Number per flower: About 10. Filament color: About Medium Green-White 157B.

*Style*.—Length: Approximately 7 to 7.5 mm. Color: About Medium Yellow-Green 145B.

*Pistil*.—Length: Approximately 8 to 9 mm. Ovary color: About Medium Green 138B.

*Anther*.—Length: Approximately 3 to 4 mm. Number: About 10. Color: About Medium Greyed-Orange 163B.

*Pollen*.—Abundance: Medium. Color: About Medium White NN155A.

*Self-compatibility*.—The cultivar has demonstrated a small degree of self-compatibility.

Fruit:

*Date of* 50% *maturity*.—About May 10$^{th}$.

*Fruit development period*.—About 75 days.

*Berry color*.—About Light Violet-Blue 97B with wax, and about Dark Black 203C without wax.

*Berry flesh color*.—About Light Green 142D.

*Berry surface wax abundance*.—Medium to high.

*Berry weight*.—1$^{st}$ Harvest: Approximately 3.7 g. 2$^{nd}$ Harvest: Approximately 3.7 g.

*Berry size*.—Height from Calyx to Scar: Approximately 14.2 mm. Diameter: Approximately 20.2 mm.

*Berry shape*.—Semi spherical to spherical.

*Fruit stem scar*.—Small, dry and with no tears.

*Calyx*.—Approximately 3 mm deep and 9 mm wide.

*Sepals*.—Typically not visible; slightly turned inward and flat when present.

*Berry firmness*.—Firm, 8/10 on berry rating scale.

*Berry flavor*.—Very sweet and floral taste.

*Berry texture*.—Crisp.

*Average brix*.—Approximately 16.83.

*Seed*.—Seed Abundance in Fruit: High. Seed Color: About Medium Greyed-Orange 165B. Seed Dry Weight: Approximately 34.7 mg per 100 seeds. Seed Size: Approximately 1.3 to 1.8 mm. Seed Quantity Average per Berry: About 24.Seed Shape: The seeds of 'CBG-23-03' are generally slightly elongated oval to slightly flattened, with a smooth surface.

*Storage qualities*.—Shelf life of 'CBG-23-04' is good. The fruit of 'CBG-23-04' was tested for storage longevity in a 39° F. refrigerated environment with low humidity for 21 days. The berries maintained quality throughout the trial, retaining firmness with minimal shrivel or leakage.

*Use/market*.—The berries of 'CBG-23-04' can be used as fresh fruit for shipping, customer-pick and processing markets. Not suitable for machine harvest.

*Disease resistance*.—Resistant to fungal diseases, but otherwise no noticeable disease resistance or susceptibility has been observed for 'CBG-23-04'.

We claim:

1. A new and distinct variety of blueberry plant named 'CBG-23-04' as illustrated and described herein.

* * * * *